US010175259B2

(12) United States Patent
Riether (10) Patent No.: US 10,175,259 B2
(45) Date of Patent: Jan. 8, 2019

(54) LABORATORY CARGO DISTRIBUTION SYSTEM, LABORATORY AUTOMATION SYSTEM AND METHOD OF OPERATING A LABORATORY CARGO DISTRIBUTION SYSTEM

(71) Applicant: Roche Diagnostics Operations., Inc., Indianapolis, IN (US)

(72) Inventor: Christian Riether, Muehltal (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/247,394

(22) Filed: Aug. 25, 2016

(65) Prior Publication Data

US 2017/0059599 A1    Mar. 2, 2017

(30) Foreign Application Priority Data

Sep. 1, 2015    (EP) .................................... 15183348

(51) Int. Cl.
*G01N 35/02*    (2006.01)
*G01N 35/04*    (2006.01)

(52) U.S. Cl.
CPC .......... *G01N 35/026* (2013.01); *G01N 35/04* (2013.01); *G01N 2035/0406* (2013.01); *G01N 2035/0465* (2013.01); *G01N 2035/0477* (2013.01)

(58) Field of Classification Search
None
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — P. Kathryn Wright
(74) *Attorney, Agent, or Firm* — Roche Diagnostics Operations, Inc.

(57) ABSTRACT

A laboratory cargo distribution system is presented. The laboratory cargo distribution system comprises a number of transport carriers, a transport plane, a number of electromagnetic actuators, a storage device and a control device. The storage device is adapted to store at least one of the number of transport carriers. A laboratory automation system comprising such a laboratory cargo distribution system and a method of operating such a laboratory cargo distribution system are also presented.

13 Claims, 4 Drawing Sheets

(56) References Cited

U.S. PATENT DOCUMENTS

| | | |
|---|---|---|
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |

FOREIGN PATENT DOCUMENTS

| | | |
|---|---|---|
| DE | 3909786 A1 | 9/1990 |
| DE | 102012000665 A1 | 8/2012 |

(56) References Cited

FOREIGN PATENT DOCUMENTS

| | | |
|---|---|---|
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-322289 A | 12/2007 |
| JP | 2007314262 A2 | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

LABORATORY CARGO DISTRIBUTION SYSTEM, LABORATORY AUTOMATION SYSTEM AND METHOD OF OPERATING A LABORATORY CARGO DISTRIBUTION SYSTEM

CROSS-REFERENCE TO RELATED APPLICATIONS

This application claims priority to EP 15183348.0 filed Sep. 1, 2015, which is hereby incorporated by reference.

BACKGROUND

The present disclosure relates to a laboratory cargo distribution system, a laboratory automation system and a method of operating a laboratory cargo distribution system.

Known laboratory cargo distribution systems are typically used in laboratory automation systems in order to distribute laboratory cargo, i.e., samples contained in sample container carriers, between different laboratory stations by means of transport carriers.

There is a need for a laboratory cargo distribution system having more functionalities than laboratory cargo distribution systems of the prior art.

SUMMARY

According to the present disclosure, a laboratory cargo distribution system a laboratory automation system and a method of operating a laboratory cargo distribution system are presented. The laboratory cargo distribution system can comprise a number of transport carriers. The transport carriers can comprise a magnetically active device and are adapted to carry laboratory cargo. The laboratory cargo distribution system can also comprise a transport plane. The transport plane can be adapted to support the transport carriers. The laboratory cargo distribution system can also comprise a number of electro-magnetic actuators. The electro-magnetic actuators can be stationary arranged below the transport plane and can be adapted to move the transport carriers on top of the transport plane by applying a magnetic move force to the transport carriers. The laboratory cargo distribution system can also comprise at least one storage device. The storage device can comprise at least one rack having at least one holder. The holder can be adapted to receive a transport carrier from the transport plane and to release the transport carrier to the transport plane. The rack can be adapted to be moved between a transfer position and a storage position. In the transfer position, the holder can be positioned to receive or to release the transport carrier. In the storage position, the transport carrier received by the holder can be removed from the transport plan. The laboratory cargo distribution system can also comprise a control device. The control device can be configured to activate the electro-magnetic actuators to apply the magnetic move force to the transport carrier such that the transport carrier can be moved into or out of the holder of the rack and to move the rack between the transfer position and the storage position.

Accordingly, it is a feature of the embodiments of the present disclosure to provide for a laboratory cargo distribution system having more functionalities than laboratory cargo distribution systems of the prior art. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory cargo distribution system is presented. The laboratory cargo distribution system can comprise a number of transport carriers, a transport plane and a number of electro-magnetic actuators. The transport carriers can comprise, in one embodiment, each of them can comprises, at least one magnetically active device. Also the transport carriers can be adapted to carry, in one embodiment each of them can be adapted to carry, at least one laboratory cargo. The transport plane can be adapted to support the transport carriers. The electro-magnetic actuators can be stationary arranged, in one embodiment in rows and columns, below the transport plane. Further, the electro-magnetic actuators can be adapted to move the transport carriers on top of the transport plane, in one embodiment each of them along an individual transport path simultaneously, by applying a magnetic move force to the transport carriers. In addition, the laboratory cargo distribution system can comprise at least one storage device. The storage device can comprise at least one rack having at least one holder. The holder can be adapted to receive a transport carrier of the number of transport carriers from the transport plane and to release the transport carrier to the transport plane. The rack can be adapted to be moved between a transfer position and a storage position. In the transfer position, the holder can be positioned, in one embodiment over the transport plane, to receive or to release the transport carrier. In the storage position, the transport carrier received by the holder can be removed from the transport plane. Furthermore, the laboratory cargo distribution system can comprise a control device. The control device can be configured to activate the electro-magnetic actuators, in one embodiment each of them individually, to apply the magnetic move force to the transport carrier such that the transport carrier can be moved into or out of the holder of the rack in the transfer position. Moreover, the control device can be configured to move the rack between the transfer position and the storage position.

The control device may be configured to activate the electro-magnetic actuators, in one embodiment each of them individually, to apply the magnetic move force to the transport carrier such that the transport carrier can be moved into or out of the holder of the rack in the transfer position only by the magnetic force. Moreover, the control device may be configured to move the rack between the transfer position and the storage position only by the magnetic force.

The laboratory cargo may comprise or be a number of sample containers and/or laboratory equipment. The sample containers can typically be designed as tubes made of glass or transparent plastic, for example, and can typically have an opening at an upper end. The sample containers can be used to contain, store and transport samples such as blood samples, urine samples or chemical samples. The laboratory equipment may comprise or be a number of analysis liquid containers. The transport plane may also be denoted as transport surface. The transport plane can support the transport carrier, what may also be denoted as carrying the transport carrier.

The electro-magnetic actuators can be energized or driven individually in order to generate a magnetic field. The magnetic field can interact with the magnetically active device of the transport carrier. By the interaction, the electro-magnetic actuators can apply the magnetic move force to the transport carrier. Hence, the transport carrier can be translationally moved in two dimensions on the transport plane. For that purpose, the electro-magnetic actuators may be arranged in a plane parallel to the transport plane. The control device can be configured to control the movement of the transport carrier along a corresponding transport path on top of the transport plane by activating the electro-magnetic actuators to apply the magnetic move force to the transport carrier.

The storage device can enable storing transport carriers, thereby, eventually leaving free space for the movement of other transport carriers on the transport plane. The rack may have two, three or more, in one embodiment five, holders. The holders may be adjacently arranged, in one embodiment in a straight line. In the storage position, the at least one holder may be positioned beside and/or above the transport plane. Moreover, the movement of the rack between the transfer position and the storage position may be perpendicular to an edge of the transport plane. When the rack is in the storage position, no transport carrier may be inserted into or removed from the holder by applying the magnetic move force to the transport carrier. The transport carrier can be inserted and fixed such as, form-fitted, form-locked or slide-press-fitted, in the holder, when it is received by the holder. Thereby, the rack can take the transport carrier received by its holder with it during the movement between the transfer position and the storage position. The storage device, the rack and/or the holder do/does not have to have actively moved components, e.g. a robot grab arm with an electric motor, for the receipt and the release of the transport carrier by the holder of the rack in the transfer position. The storage device, the rack or the holder may also be denoted as a passive component. A movement of the transport carrier towards or into the holder caused by the electro-magnetic actuators may be sufficient for the receipt and a movement of the transport carrier out of the holder caused by the electro-magnetic actuators may be sufficient for the release. Since the laboratory cargo is stored by its assigned transport carrier in the storage device, only the rack may need to be moved into its transfer position and the transport carrier to be released, when the laboratory cargo may need to be brought back to the transport plane. This may be beneficial for a throughput of the laboratory cargo distribution system. The laboratory cargo distribution system may also be denoted high performance archive.

A method of operating a laboratory cargo distribution system as described above is also presented. The method can comprise (a) activating the electro-magnetic actuators to apply the magnetic move force to the transport carrier such that the transport carrier is moved or inserted into the holder of the rack in the transfer position. The method can further comprise (b) moving the rack from the transfer position to the storage position and (c) moving the rack from the storage position to the transfer position. In addition, the method can comprise (d) activating the electro-magnetic actuators to apply the magnetic move force to the transport carrier such that the transport carrier is moved out or removed from the holder of the rack in the transfer position. The steps (a) to (d) can be performed or executed in the mentioned order. Alternatively, the steps may be performed in the order (c), (d), (a) and (b).

According to an embodiment, the rack can comprise at least one magnetically active device. Furthermore, the rack can be adapted to be moved at least in part over, in one embodiment on, the transport plane, in particular parallel to the transport plane, between the transfer position and the storage position. Moreover, the control device can be configured to activate the electro-magnetic actuators to apply a magnetic move force to the rack such that the rack can be moved over the transport plane between the transfer position and the storage position. Thereby, the storage device, the rack or the holder may not have to have electric motors for the movement of the rack between the transfer position and the storage position. The transport plane may be adapted to support at least a part of the rack. Furthermore, the rack may comprise a sliding surface for its movement on the transport plane.

According to one embodiment, step (b) can comprise activating the electro-magnetic actuators to apply the magnetic move force to the rack such that the rack is moved from the transfer position to the storage position and step (c) can comprise activating the electro-magnetic actuators to apply the magnetic move force to the rack such that the rack is moved from the storage position to the transfer position.

According to one embodiment, the storage device can comprise a storage device housing. The storage device housing can be arranged adjacent to the transport plane. The rack in the storage position can be arranged at least with its at least one holder inside the storage device housing and the rack in the transfer position can be at least partially arranged with one holder outside the storage device housing. The magnetically active device of the rack can be arranged at a region of the rack facing towards the transport plane. So, the transport carrier received by the holder may be protected by the storage device housing, when the rack is in the storage position.

According to one embodiment, the storage device housing can comprise a linear guidance. The linear guidance can be adapted to linearly guide the movement of the rack between the transfer position and the storage position. Hence, the rack may also be denoted as drawer rack. The linear guidance may comprise at least one slide bearing.

According to one embodiment, the storage device housing can comprise air conditioning. The air conditioning can be adapted to cool the transport carrier received in the holder of the rack in the storage position. So, for example, blood samples carried by the transport carriers can be stored in the storage device for a relatively long time, until these samples may deteriorate. The air conditioning may be adapted to cool the transport carriers indirectly by cooling the atmosphere inside of the storage device housing. Additionally, the air conditioning may comprise a thermometer for a feedback control of the temperature of the transport carrier and/or the temperature of the atmosphere inside of the storage device housing. The storage device may also be denoted as archive or refrigerator. The air conditioning may be adapted to cool transport carriers being located on the transport plane and/or in other regions of the laboratory cargo distribution system as well.

According to one embodiment, the holder can comprise a fixation device and the transport carrier can comprise complementary fixation device. The fixation device and the complementary fixation device can be adapted to mechanically fix the transport carrier to the holder, if or when the transport carrier is received in the holder, for example, by forming a form lock fix or form-locked join. The fixation device may comprise at least one finger or fork and the complementary fixation device may comprise at least one recess. The finger or fork can be adapted to engage with the recess.

The storage device may comprise a plurality of racks adjacently arranged, for example, along the edge of the transport plane.

According to one embodiment, the laboratory cargo distribution system can comprises at least one further transport plane, a further number of electro-magnetic actuators and at least one vertical conveying device. The further transport plane can be arranged vertically different relative to the transport plane and may be designed similar or even identical to the transport plane. The further number of electro-magnetic actuators can be stationary arranged below the further transport plane and may be designed similar or even identical to the number of electro-magnetic actuators. The vertical conveying device can be adapted to transport the transport carrier between the transport plane and the further transport plane. Furthermore, the storage device can comprise at least one further rack. The further rack can be arranged vertically different relative to the rack accordingly to the further transport plane and may be designed similar or even identical to the rack. Moreover, the control device can be configured to control the further number of electro-magnetic actuators as the number of electro-magnetic actuators, the further rack as the rack and the vertical conveying device such that the transport carrier can be transported between the transport plane and the further transport plane. Hence, the laboratory cargo distribution system may be constructed in a space saving way for a laboratory. The vertical conveying device may also be denoted elevator. The vertical conveying device may comprise one or more conveying planes and correspondingly one or more electro-magnetic actuators stationary arranged below the conveying planes. The conveying planes may be designed similar or even identical to the transport plane. The electro-magnetic actuators of the vertical conveying device may be designed similar or even identical to the number of electro-magnetic actuators. Accordingly, the control device may be configured to control electro-magnetic actuators of the vertical conveying device as the number of electro-magnetic actuators and a movement of the conveying planes between the transport plane and the further transport plane, such that the transport carrier can be transported between the transport plane and the further transport plane. The number of transport carriers may be distributed at least over the transport plane, the further transport plane, the vertical conveying device and the storage device.

In one embodiment, the vertical conveying device may be a paternoster elevator. The paternoster elevator may comprise one or more conveying planes and correspondingly one or more electro-magnetic actuators stationary arranged below the conveying planes. The conveying planes may be designed similar or even identical to the transport plane. The electro-magnetic actuators of the vertical conveying device may be designed similar or even identical to the number of electro-magnetic actuators. Additionally, the paternoster elevator may comprise a circulating device, which can be realized for the purpose of rotatingly moving or circulating the conveying planes and the electro-magnetic actuators in operation between the transport plane and the further transport plane. The conveying planes can or remain continuously horizontally aligned during the rotating movement. A circulating path of the conveying planes may comprise a first vertical portion and a second vertical portion which can be parallel thereto. The portions can extend operation between the transport plane and the further transport plane. In operation, the circulating device can move the conveying planes along the first vertical portion from the transport plane to the further transport plane and can additionally move the conveying planes along the second vertical portion from the further transport plane to the transport plane. Accordingly, the control device may be configured to control electro-magnetic actuators of the vertical conveying device as the number of electro-magnetic actuators and the circulating device for a movement of the conveying planes between the transport plane and the further transport plane, such that the transport carrier can be transported between the transport plane and the further transport plane. Further details of the paternoster elevator are disclosed in the European patent application EP 14162940.2, the content of which is incorporated by reference insofar.

According to one embodiment, the storage device system can comprise at least one further rack and a circulating device. The further rack can be arranged vertically and/or horizontally spaced relative to the rack and may be designed similar or even identical to the rack. The circulating device can be realized for the purpose of rotatingly moving or circulating the rack and the further rack in operation along a circulating path from the transport plane vertically and/or horizontally away and subsequently back to the transport plane. The rack and the further rack can or remain continuously horizontally aligned during the rotating movement. Accordingly, the control device can be configured to control the circulating device, such that the rack and the further rack can be moved along the circulating path. Either the rack or the further rack may be positioned at the transport plane, such that it can be moved between the storage position and the transfer position. When the rack or the further rack is positioned distant from the transport plane, it may not be moved between the storage position and the transfer position. This may be a space saving configuration of the storage device.

A laboratory automation system is also presented. The laboratory automation system can comprise a number of laboratory stations such as, for example, pre-analytical stations, analytical stations and/or post-analytical stations. Furthermore, the laboratory automation system can comprise a laboratory cargo distribution system as described above. The laboratory cargo distribution system can be adapted to distribute the transport carriers and/or laboratory cargo between the laboratory stations. The laboratory stations may be arranged adjacent to the laboratory cargo distribution system. Pre-analytical stations may be adapted to perform any kind of pre-processing of samples, sample containers and/or transport carriers. Analytical stations may be adapted to use a sample or part of the sample and a reagent to generate a measuring signal. The measuring signal can indicate if and in which concentration, if any, an analyte is existing. Post-analytical stations may be adapted to perform any kind of post-processing of samples, sample containers and/or transport carriers. The pre-analytical, analytical and/or post-analytical stations may comprise at least one of a decapping station, a recapping station, an aliquot station, a centrifugation station, a further archiving station, a pipetting station, a sorting station, a tube type identification station, a sample quality determining station, an add-on buffer station, a liquid level detection station, and a sealing/desealing station. Additionally, they may comprise at least one pushing station, belt station, conveying system station and/or gripper station for moving the laboratory cargo to or from the transport carrier.

Figure 1:
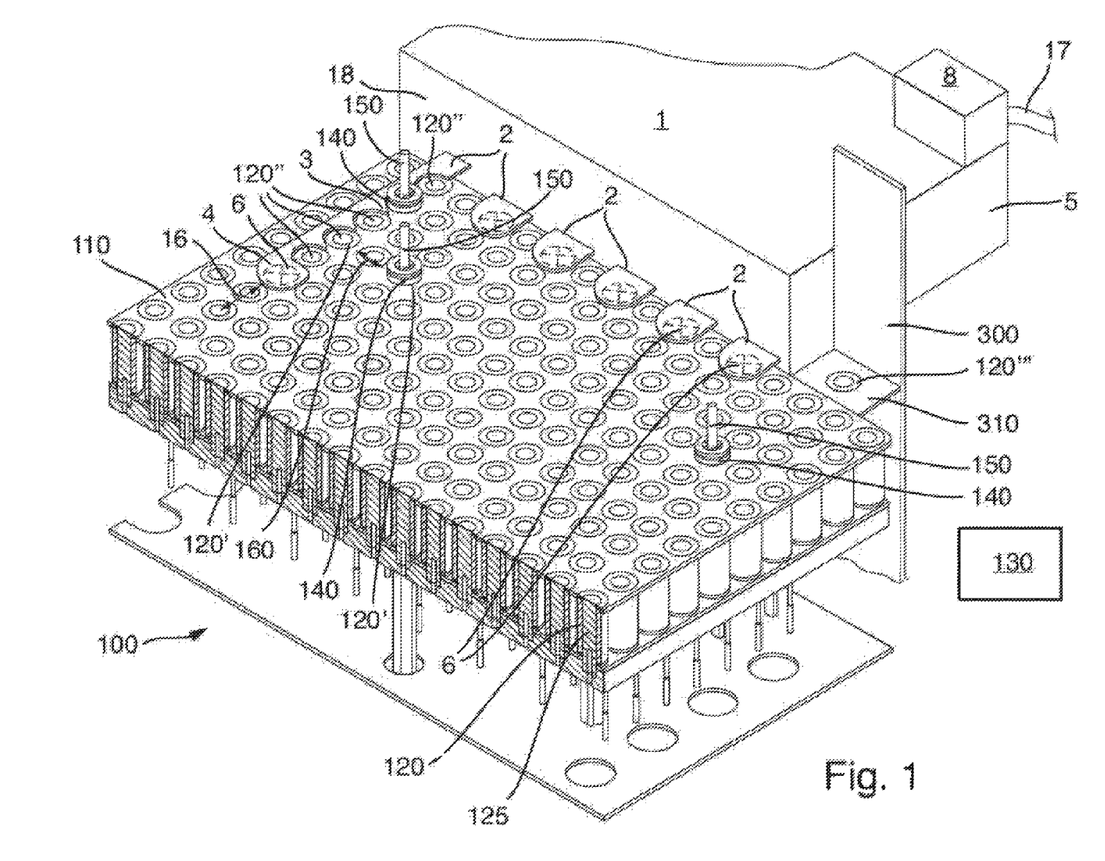
FIG. 1 illustrates a perspective view of a laboratory cargo distribution system according to an embodiment of the present disclosure.

Referring initially to FIG. 1, FIG. 1 shows a laboratory cargo distribution system 100. The laboratory cargo distribution system 100 can comprise a number of electro-magnetic actuators 120, 120', 120" and a transport plane 110. The number of electro-magnetic actuators 120, 120', 120" can be stationary arranged below the transport plane 110. The electro-magnetic actuators 120, 120', 120" can be quadratically arranged in a grid or matrix having rows and columns in a plane parallel to the transport plane 110. Furthermore, the electro-magnetic actuators 120, 120', 120" can be implemented as solenoids having a solid ferromagnetic core 125.

Figure 2:
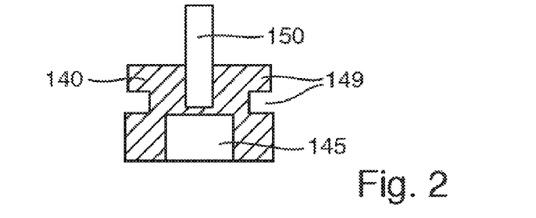
FIG. 2 illustrates a longitudinal section view of a transport carrier of FIG. 1 according to an embodiment of the present disclosure.

Moreover, the laboratory cargo distribution system 100 can comprise a number of transport carriers 140. The transport plane 110 can be adapted to support or carry the transport carriers 140. The transport carriers 140 can comprise a sliding surface at their underside. The sliding surface can be adapted to be in contact with the transport plane 110 and can enable performing movements of the transport carriers 140 on the transport plane 110. The transport carriers 140 can be positioned on the transport plane 110. While it can be understood that a plurality of sample container carriers 140 can be positioned on the transport plane 110, due to simplicity only three transport carriers 140 are depicted in FIG. 1. The transport carriers 140 can be adapted to carry a laboratory cargo 150, which is, in this embodiment, a sample container. The sample containers can be used to contain, store and transport samples such as blood samples, urine samples or chemical samples. The sample containers can be designed as tubes made of glass or transparent plastic and can have an opening at an upper end. In alternative embodiments the laboratory cargo may be laboratory equipment. The laboratory equipment may comprise or be a number of analysis liquid containers. Further, the transport carriers 140 can comprise a magnetically active device 145, as depicted in FIG. 2, which can be, in this embodiment, a permanent magnet. In alternative embodiments, the magnetically active device may be an electro-magnetic actuator.

The electro-magnetic actuators 120, 120', 120" can be adapted to move the transport carriers 140 on top of the transport plane 110, in one embodiment, each of them along an individual transport path simultaneously, by applying a magnetic move force to the transport carriers 140. In detail, the electro-magnetic actuators 120, 120', 120" can be energized or driven individually in order to generate a magnetic field for each transport carrier 140. The magnetic field can interact with the magnetically active device 145 of the respective transport carrier 140. By the interaction, the electro-magnetic actuators 120, 120', 120" can apply the magnetic move force to the transport carrier 140. Hence, the transport carriers 140 can be translationally moved in two dimensions on the transport plane 110.

Further, the laboratory cargo distribution system 100 can comprise a control device 130. The control device 130 can be configured to control the movements of the transport carriers 140 on the transport plane 110 by activating and controlling or driving the electro-magnetic actuators 120, 120', 120" such that the transport carriers 140 can independently and simultaneously move along the transport paths.

Furthermore, the laboratory cargo distribution system 100 can comprise a number of not-shown Hall-sensors. The Hall-sensors can be arranged such that positions of the transport carriers 140 on the transport plane 110 can be detected.

In addition, the laboratory cargo distribution system 100 can comprises at least one storage device 1. The storage device 1 can comprise a number of racks 2. In this embodiment, the storage device 1 can comprise a plurality of racks 2 adjacently arranged such as, for example, along an edge of the transport plane 110. The racks 2 can have a number of holders 3, which in this embodiment, can be five. Additionally, in this embodiment, the holders 3 of a rack 2 can be adjacently arranged in a straight line with a distance corresponding to a distance between two adjacent electro-magnetic actuators 120, 120', 120". The holders 3 can be adapted to receive a transport carrier 140 from the transport plane 110 and to release the transport carrier 140 to the transport plane 110. The racks 2 can be adapted to be moved between a transfer position and a storage position, in this embodiment, perpendicular to the edge of the transport plane 110. Thereby, the racks 2 can take the transport carriers 140 received by the holders 3 with them during the movement between the transfer position and the storage position. In the transfer position, at least one of the holders 3 can be positioned over the transport plane 110 to receive or to release the transport carrier 140, as depicted for the holders 3 of the lower rack 2 in FIG. 4. In the storage position, the transport carrier 140 received by the holder 3 can be removed from the transport plane 110, as depicted for the holders 3 of the upper rack 2 in FIG. 4. The transport carriers 140 received by the holders 3 of the upper rack 2 in the storage position in FIG. 4 can be positioned beside the transport plane 110. In alternative embodiments, a transport carrier received by a holder of a rack in the storage position may be positioned above the transport plane. The storage device 1 can enable leaving free space for the movement of other transport carriers 140 on the transport plane 110.

The control device 130 can be configured to activate the electro-magnetic actuators 120, 120' to apply the magnetic move forces to the transport carriers 140 such that the transport carriers 140 can be moved into or out of the holders 3 of the racks 2 in the transfer position. Moreover, the control device 130 can be configured to move the racks 2 between their transfer positions and their storage positions.

In FIG. 1, the electro-magnetic actuators 120' can be activated successively to apply the magnetic move force to and/or to successively attract the, in FIG. 1 lower left, transport carrier 140 such that the transport carrier 140 can be moved or inserted into its respective holder 3 of the rack 2 in the transfer position, as denoted by arrow 160. This action can correspond to step (a) of the method of operating the laboratory cargo distribution system 100 in FIG. 5. The movement of the transport carrier 140 towards or into the holder 3 caused by the electro-magnetic actuators 120' can be sufficient for the receipt. The upper left transport carrier 140 in FIG. 1, already received by the holder 3, can be inserted and fixed such as, for example, form-fitted, form-locked or slide-press-fitted, in its respective holder 3.

When the lower left transport carrier 140 is received by its respective holder 3, the left rack 2 in FIG. 1 may be moved from the transfer position to the storage position, as denoted by arrow 16. This action can correspond to step (b) in FIG. 5. When the left rack 2 is in the storage position, no transport carrier 140 may be inserted into or removed from its holder 3 by applying the magnetic move force to the transport carrier 140.

In detail, the racks 2 can comprise at least one magnetically active device 4, which, in this embodiment, can be a permanent magnet. In alternative embodiments, the magnetically active device may be an electro-magnetic actuator. The magnetically active device 4 can be sideways respectively parallel to the transport plane 110 displaced to the holders 3. The racks 2 can be adapted to be moved at least in part over the transport plane 110 such as parallel to the transport plane 110, between the respective transfer position and the respective storage position. In detail, the transport plane 110 can be adapted to support or carry at least a part of the racks 2. Furthermore, the racks 2 can comprise a sliding surface at their underside in the region of the magnetically active device 4 for their movement on the transport plane 110. The control device 130 can be configured to activate the electro-magnetic actuators 120" to apply a magnetic move force to a corresponding rack 2 such that the rack 2 can be moved over the transport plane 110 between the transfer position and the storage position. When the lower left transport carrier 140 in FIG. 1 is received by its respective holder 3, the electro-magnetic actuators 120" may be activated successively to apply the magnetic move force to and/or to successively attract the left rack 2 in FIG. 1 such that the rack 2 can be moved from the transfer position to the storage position. The electro-magnetic actuators 120" arranged below the transport plane 110 can be sufficient for causing the movement of the rack 2 from its transfer position to its storage position. By the Hall-sensors, the positions of the racks 2 on the transport plane 110 can be detected.

When the transport carriers 140 in the left rack 2 in its storage position can be brought back to the transport plane 110, the left rack 2 can be moved from the storage position to the transfer position, as denoted by arrow 16 in FIG. 1. This action can correspond to step (c) in FIG. 5. In detail, step (c) can comprise activating the electro-magnetic actuators 120" to apply the magnetic move force to the rack 2 such that the rack 2 can be moved from the storage position to the transfer position. The electro-magnetic actuators 120" arranged below the transport plane 110 can be sufficient for causing the movement of the rack 2 from its storage position to its transfer position. Afterwards the electro-magnetic actuators 120' can be activated successively to apply the magnetic move force to and/or to successively attract the, in FIG. 1 lower left, transport carrier 140 such that the transport carrier 140 can be moved out or removed from its respective holder 3 of the rack 2 in the transfer position, as denoted by arrow 160. This action can correspond to step (d) in FIG. 5. The movement of the transport carrier 140 out of the holder 3 caused by the electro-magnetic actuators 120' can be sufficient for the release.

Because the electro-magnetic actuators 120', 120" arranged below the transport plane 110 can be sufficient for the receipt and the release of the transport carrier 140 by the holder 3 and for the movement of the rack 2 between the transfer position and the storage position, each of the storage device 1, the rack 2 or the holder 3 may be denoted as a passive component.

Figure 5:
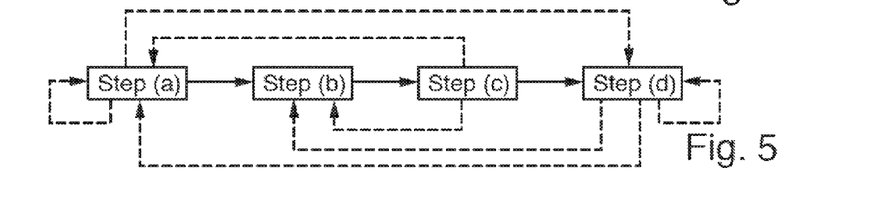
FIG. 5 illustrates a method of operating the laboratory cargo distribution system of FIG. 1 according to an embodiment of the present disclosure.

The steps (a) to (d) can be performed or executed in the mentioned order. Alternatively, the steps may be performed in a different order, e.g. (c), (d), (a) and (b), as indicated in FIG. 5 by dashed arrows.

Figure 4:
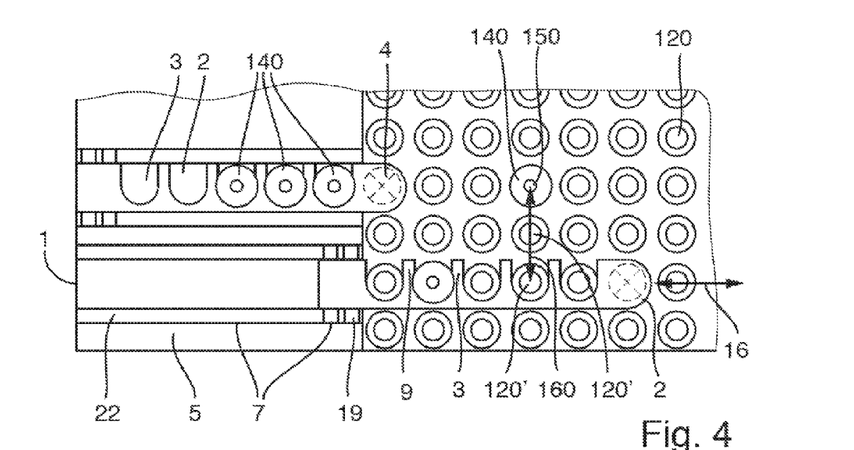
FIG. 4 illustrates a cross section view of the laboratory cargo distribution system of FIG. 1 according to an embodiment of the present disclosure.

Constructional wise, the storage device 1 can comprise a storage device housing 5. The storage device housing 5 can be arranged adjacent to the transport plane 110. The racks 2 in their respective storage positions can be arranged with their holders 3 inside the storage device housing 5, as depicted in FIGS. 1 and 4. The left rack 2 in FIG. 1 in the transfer position can at least be partially arranged with all of its holders 3 outside the storage device housing 5. The magnetically active devices 4 of the racks 2 can be arranged at regions 6 of the racks 2 facing towards the transport plane 110 and can always be arranged outside the storage device housing 5. The regions 6 can have a footprint on the transport plane 110 similar to a footprint of the transport carriers 140. So, the transport carriers 140 received by the holders 3 may be protected by the storage device housing 5, when the corresponding racks 2 are in the storage position. In alternative embodiments, a rack in the storage position may be completely arranged inside the storage device housing. Additionally, the storage device 1 can comprise a curtain 18 such as, for example, an air curtain, arranged at a side of the storage device housing facing towards the transport plane 110.

Figure 3:
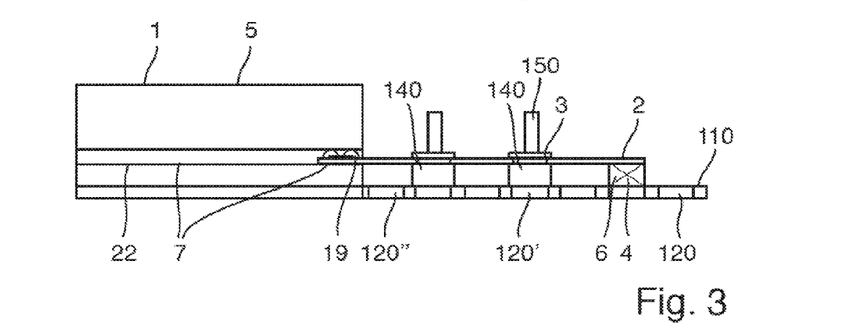
FIG. 3 illustrates a longitudinal section view of the laboratory cargo distribution system of FIG. 1 according to an embodiment of the present disclosure.

The storage device housing 5 can comprise a number of linear guidance 7, as depicted in FIGS. 3 and 4. The linear guidance 7 can be adapted to linearly guide the movement of the racks 2 between the transfer position and the storage position. Hence, the racks 2 may also be denoted as drawer racks. In this embodiment, the linear guidance 7 can comprise rails 22 and slide bearings or wheels 19.

Figure 7A:
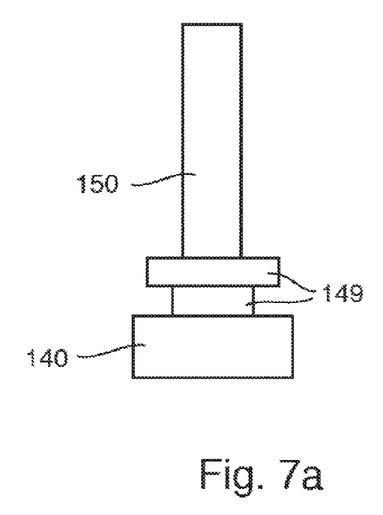
FIG. 7a illustrates a transport carrier according to an embodiment of the present disclosure.
Figure 7B:
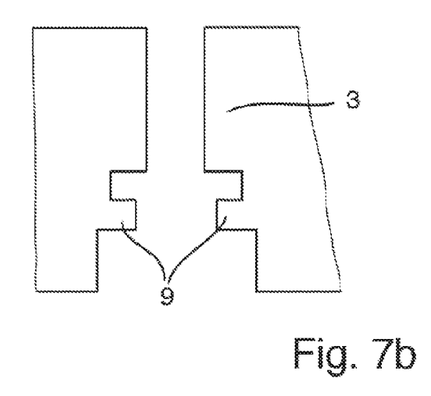
FIG. 7b illustrates a longitudinal section view of a holder for the transport carrier of FIG. 7a according to an embodiment of the present disclosure.
Figure 7C:
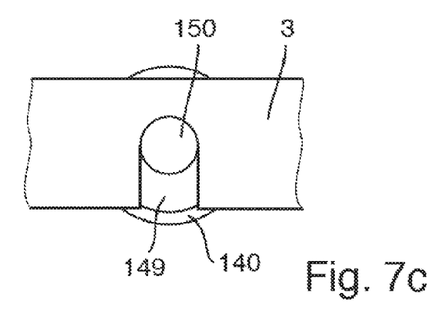
FIG. 7c illustrates a top view of the transport carrier of FIG. 7a received by the holder of FIG. 7b according to an embodiment of the present disclosure.

The holders 3 can comprise a fixation device 9 and the transport carriers 140 can comprise a complementary fixation device 149, as depicted in FIGS. 2 and 4. The fixation device 9 and the complementary fixation device 149 can be adapted to mechanically fix a respective transport carrier 140 to its assigned holder 3, when the transport carrier 140 is received in the holder 3 such as, for example, by forming a form lock fix or form-locked join. In this embodiment, the fixation device 9 can comprise at least one finger, or fork, and the complementary fixation device 149 can comprise at least one recess. The finger, or fork, can be adapted to engage with the recess. In FIGS. 7a, 7b and 7c, another embodiment of a transport carrier 140 with its complementary fixation device 149 and another embodiment of a holder 3 with its fixation device 9 according to the shape of the transport carrier 140 with laboratory cargo 150 is shown.

Moreover, the storage device housing 5 in FIG. 1 can comprise air conditioning 8. The air conditioning 8 can be adapted to cool the transport carriers 140 received in the holders 3 of the racks 2 in their storage position. In this embodiment, the air conditioning 8 can be adapted to cool the transport carriers 140 indirectly by cooling the atmosphere inside of the storage device housing 5. The storage device 1 may also be denoted as archive or refrigerator. The air conditioning 8 can be adapted to cool transport carriers 140 located on the transport plane 110 and other regions of the laboratory cargo distribution system 100 as well by the air pipe 17, as depicted in FIG. 6.

Figure 6:
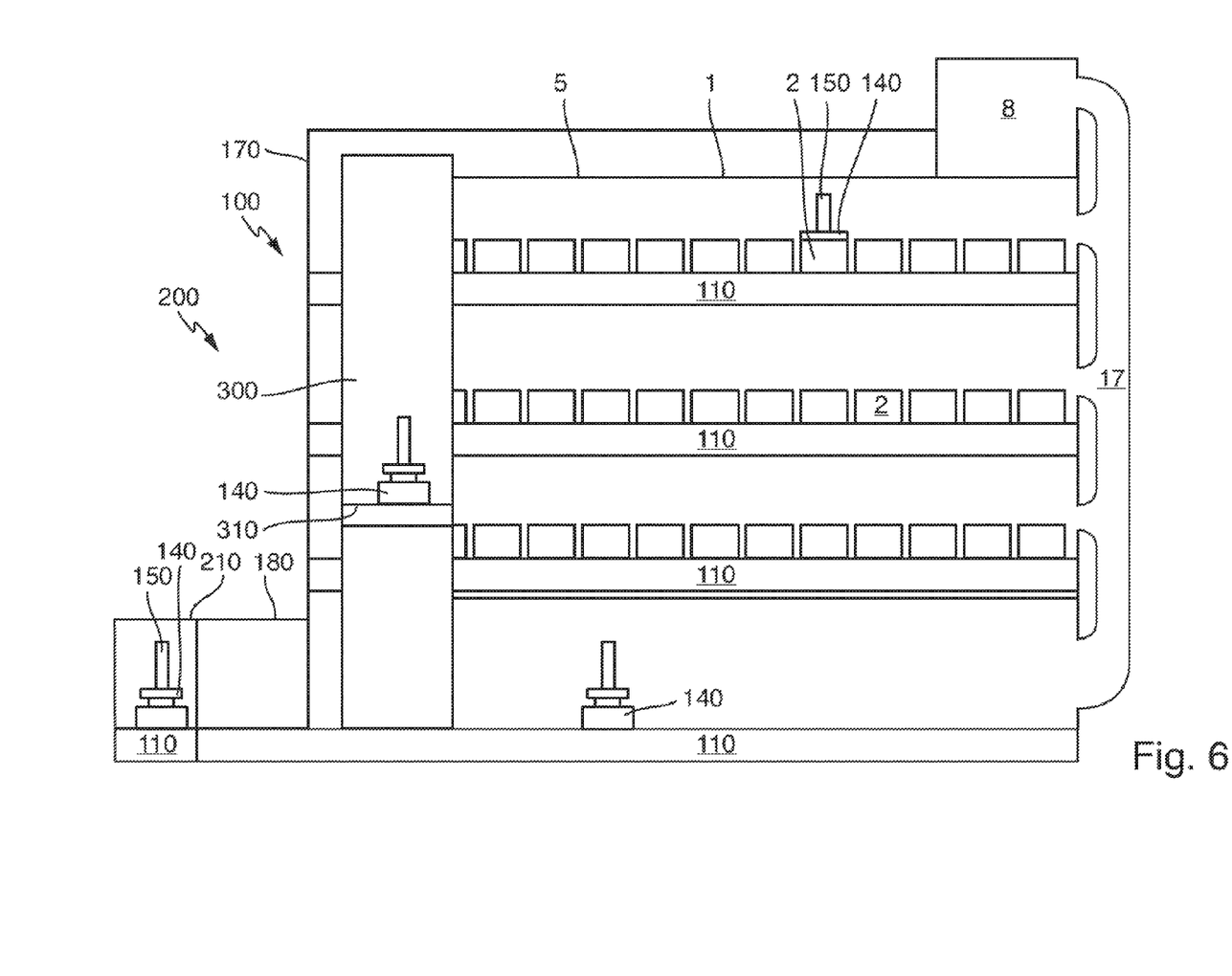
FIG. 6 illustrates a longitudinal section view of a laboratory automation system comprising the laboratory cargo distribution system of FIG. 1 according to an embodiment of the present disclosure.

The laboratory cargo distribution system 100 can comprise a number of further transport planes 110, a further number of electro-magnetic actuators 120, 120', 120" and at least one vertical conveying device 300, as depicted in FIG. 6, such as, for example, a paternoster elevator. The further transport planes 110 can be arranged vertically different relative to the transport plane 110 and can be designed similar or even identical to the transport plane 110. The further number of electro-magnetic actuators 120, 120', 120" can be stationary arranged below the further transport planes 110 and can be designed similar or even identical to the number of electro-magnetic actuators 120, 120', 120". The vertical conveying device 300 can be adapted to transport at least one of the transport carriers 140 between the transport plane 110 and the further transport planes 110. Furthermore, the storage device 1 can comprise a number of further racks 2. The further racks 2 can be arranged vertically different relative to the racks 2 accordingly to the further transport planes 110 and can be designed similar or even identical to the racks 2. Moreover, the control device 130 can be configured to control the further number of electro-magnetic actuators 120, 120', 120" as the number of electro-magnetic actuators 120, 120', 120", the further racks 2 as the racks 2 and the vertical conveying device 300 such that at least one transport carrier 140 can be transported between the transport plane 110 and the further transport planes 110.

In this embodiment, the vertical conveying device 300 can comprise at least one conveying plane 310 and, correspondingly, at least one electro-magnetic actuator 120''' stationary arranged below the conveying plane 310. The at least one conveying plane 310 can be designed similar or even identical to the transport planes 110. Accordingly, the control device 130 can be configured to control the electro-magnetic actuator 120''' of the vertical conveying device 300 as the number of electro-magnetic actuators 120, 120', 120" and a movement of the conveying plane 310 between the transport plane 110 and the further transport planes 110, such that the transport carrier 140 can be transported between the transport plane 110 and the further transport planes 110. In addition, the conveying plane 310 can comprise at least one not-shown Hall-sensor such that the transport carrier 140 on the conveying plane 310 can be detected.

In this embodiment, the topmost transport plane may be denoted as the transport plane 110 and the three transport planes below it may be denoted as the further transport planes 110, one of them without access to the storage device 1 and its racks 2, respectively. This further transport plane 110 may be denoted main transport plane. Furthermore, the laboratory cargo distribution system 100 can comprise a laboratory cargo distribution system housing 170 surrounding at least the transport plane 110 and the further transport planes 110 and the vertical conveying device 300. The air conditioning 8 can be adapted to cool transport carriers 140 located inside the laboratory cargo distribution system housing 170 via the air pipe 17. Possible heat from the air conditioning 8 can be lead to the outside of the storage device housing 5 and to the outside of the laboratory cargo distribution system housing 170. The main transport plane 110 may be useful just for keeping transport carriers 140 cool.

Moreover, the laboratory cargo distribution system 100 can comprise an additional transport plane 110, an additional number of not-shown electro-magnetic actuators and an air-lock 180. This additional transport plane 110 can be adjacently arranged to the laboratory cargo distribution system housing 170 and the main transport plane 110, respectively. The additional transport plane 110 can be designed similar or even identical to the transport plane 110 and the further transport planes 110. The additional number of electro-magnetic actuators can be stationary arranged below the additional transport plane 110 and can be designed similar or even identical to the number of electro-magnetic actuators 120, 120', 120". The air-lock 180 can be adapted to enable a movement of at least one of the number of transport carriers 140 from the inside of the laboratory cargo distribution system housing 170 to the outside transport plane 110 and/or vice versa. Additionally, the air-lock 180 can be adapted to lock the inside of the laboratory cargo distribution system housing 170 from the outside, when no movement is demanded. Moreover, the control device 130 can be configured to control the additional number of electro-magnetic actuators as the number of electro-magnetic actuators 120, 120', 120" and the air-lock 180 such that the transport carrier 140 can be moved from the inside of the laboratory cargo distribution system housing 170 to the outside transport plane 110 and/or vice versa.

A decapping and/or recapping station, a sealing and/or desealing station and/or a transport carrier and/or laboratory cargo identification station, e.g. a barcode reader, may be integrated into the air-lock 180. The decapping and/or a recapping station and the sealing and/or desealing station may be useful for sample containers in form of tubes having an opening at an upper end.

Since laboratory cargo 150 can be stored by its assigned transport carrier 140 in the storage device 1, it can be easy to bring the laboratory cargo 150 to the additional transport plane 110 outside of the laboratory cargo distribution system housing 170, when the laboratory cargo 150 is needed. This can be beneficial for a throughput of the laboratory cargo distribution system 100. The laboratory cargo distribution system 100 may also be denoted high performance archive.

The laboratory cargo distribution system 100 can be part of a laboratory automation system 200. The laboratory automation system 200 can comprise the laboratory cargo distribution system 100 and a number of laboratory stations 210 in form of a pre-analytical, analytical and/or post-analytical laboratory station arranged adjacent to the laboratory cargo distribution system 100. Self-evidently, more than the one laboratory station 210 depicted in FIG. 6 may be comprised in the laboratory automation system 200. The laboratory cargo distribution system 100 can be adapted to distribute the transport carriers 140 and/or the laboratory cargo 150 by the transport carriers 140 between the laboratory stations 210. The laboratory station 210 can be positioned adjacent to the additional transport plane 110 such that the transport carriers 140 can be used to transport laboratory cargo 150 or its content to it.

As the illustrated and discussed embodiments reveal, a laboratory cargo distribution system comprising a number of transport carriers, a transport plane, a number of electro-magnetic actuators, a storage device and a control device can be provided. The storage device can be adapted to store at least one of the number of transport carriers, thereby, eventually leaving free space for the movement of other transport carriers on the transport plane. The storage device may not have to have actively moved components for the storage of the at least one of the number of transport carriers; the use of the electro-magnetic actuators may be sufficient for the storage. Furthermore, a laboratory automation system comprising such a laboratory cargo distribution system and a method of operating such a laboratory cargo distribution system can be provided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory cargo distribution system, the laboratory cargo distribution system comprising:
　a number of transport carriers, wherein the transport carriers comprise a magnetically active device and are configured to carry laboratory cargo;
　a transport plane, wherein the transport plane is configured to support the transport carriers;
　a number of electro-magnetic actuators, wherein the electro-magnetic actuators are stationary arranged below the transport plane and are configured to move the transport carriers on top of the transport plane by applying a magnetic move force to the transport carriers;
　at least one storage device, wherein the storage device comprises at least one rack having at least one holder, wherein the holder is configured to receive a transport carrier from the transport plane and to release the transport carrier to the transport plane, wherein the rack comprises a magnetically active device and is configured to be moved at least in part over the transport plane between the transfer position and the storage position, wherein in the transfer position the holder is positioned to receive or to release the transport carrier, wherein in the storage position the transport carrier received by the holder is removed from the transport plane, wherein the storage device comprises a storage device housing, wherein the storage device housing is arranged adjacent to the transport plane, wherein the storage device housing comprises a linear guidance, wherein the linear guidance is configured to linearly guide the movement of the rack between the transfer position and the storage position, wherein the rack in the storage position is arranged inside the storage device housing and the rack in the transfer position is at least partially arranged outside the storage device housing, and wherein the magnetically active device of the rack is arranged at a region of the rack facing towards the transport plane; and
　a control device, wherein the control device is configured to activate the electro-magnetic actuators to apply the magnetic move force to the transport carrier such that the transport carrier is moved into or out of the holder of the rack and to apply a magnetic move force to the rack such that the rack is moved over the transport plane between the transfer position and the storage position.

2. The laboratory cargo distribution system according to claim 1, wherein the storage device housing comprises an air conditioning.

3. The laboratory cargo distribution system according to claim 2, wherein the air conditioning is configured to cool the transport carrier received in the holder of the rack in the storage position.

4. The laboratory cargo distribution system according to claim 1, wherein the holder comprises a fixation device and the transport carrier comprises a complementary fixation device.

5. The laboratory cargo distribution system according to claim 4, wherein the fixation device and the complementary fixation device are configured to mechanically fix the transport carrier to the holder if the transport carrier is received in the holder.

6. The laboratory cargo distribution system according to claim 1, further comprising,
　a further transport plane, wherein the further transport plane is arranged vertically different relative to the transport plane;
　a further number of electro-magnetic actuators, wherein the further number of electro-magnetic actuators is stationary arranged below the further transport plane; and
　at least one vertical conveying device, wherein the vertical conveying device is configured to transport the transport carrier between the transport plane and the further transport plane.

7. The laboratory cargo distribution system according to claim 6, wherein the storage device comprises a further rack, wherein the further rack is arranged vertically different relative to the rack, and wherein the control device is configured to control the further number of electro-magnetic actuators, the further rack, and the vertical conveying device such that the transport carrier is transported between the transport plane and the further transport plane.

8. A laboratory automation system, the laboratory automation system comprising:
　a number of laboratory stations; and
　a laboratory cargo distribution system according to claim 1, wherein the laboratory cargo distribution system is configured to distribute laboratory cargo between the laboratory stations.

9. The the laboratory automation system according to claim 8, wherein the laboratory stations comprise pre-analytical stations, analytical stations and/or post-analytical stations.

10. A method of operating a laboratory cargo distribution system according to claim 1, the method comprising:
　(a) activating the electro-magnetic actuators to apply the magnetic move force to the transport carrier such that the transport carrier is moved into the holder of the rack in the transfer position;
　(b) moving the rack from the transfer position to the storage position;
　(c) moving the rack from the storage position to the transfer position; and
　(d) activating the electro-magnetic actuators to apply the magnetic move force to the transport carrier such that the transport carrier is moved out the holder of the rack in the transfer position.

11. The method of operating a laboratory cargo distribution system according to claim 10, wherein the rack comprises a magnetically active device and is configured to be moved at least in part over the transport plane between the transfer position and the storage position and wherein the control device is configured to activate the electro-magnetic actuators to apply a magnetic move force to the rack such that the rack is moved over the transport plane between the transfer position and the storage position, wherein step (b) comprises activating the electro-magnetic actuators to apply the magnetic move force to the rack such that the rack is moved from the transfer position to the storage position and step (c) comprises activating the electro-magnetic actuators to apply the magnetic move force to the rack such that the rack is moved from the storage position to the transfer position.

12. The method of operating a laboratory cargo distribution system according to claim 11, wherein step (b) comprises activating the electro-magnetic actuators to apply the magnetic move force to the rack such that the rack is moved from the transfer position to the storage position.

13. The method of operating a laboratory cargo distribution system according to claim 12, wherein step (c) comprises activating the electro-magnetic actuators to apply the magnetic move force to the rack such that the rack is moved from the storage position to the transfer position.

* * * * *